(12) United States Patent
von Jako

(10) Patent No.: US 8,475,470 B2
(45) Date of Patent: Jul. 2, 2013

(54) PERCUTANEOUS REGISTRATION APPARATUS AND METHOD FOR USE IN SURGICAL NAVIGATION

(75) Inventor: Ronald A. von Jako, Saugus, MA (US)

(73) Assignee: General Electric Company, Schenectady, NY (US)

(*) Notice: Subject to any disclaimer, the term of this patent is extended or adjusted under 35 U.S.C. 154(b) by 1491 days.

(21) Appl. No.: 11/614,459

(22) Filed: Dec. 21, 2006

(65) Prior Publication Data
US 2008/0154285 A1  Jun. 26, 2008

(51) Int. Cl.
*A61B 19/00* (2006.01)
(52) U.S. Cl.
USPC ........................................... 606/130
(58) Field of Classification Search
USPC .......... 606/130, 426, 53, 74, 151, 207, 86 R, 606/300–331; 600/426–429
See application file for complete search history.

(56) References Cited

U.S. PATENT DOCUMENTS

| | | | |
|---|---|---|---|
| 4,611,582 A * | 9/1986 | Duff | 606/258 |
| 6,226,548 B1 * | 5/2001 | Foley et al. | 600/426 |
| 6,993,374 B2 * | 1/2006 | Sasso | 600/426 |
| RE39,133 E | 6/2006 | Clayton et al. | |
| 7,063,705 B2 * | 6/2006 | Young et al. | 606/86 R |
| 7,107,091 B2 * | 9/2006 | Jutras et al. | 600/429 |
| 8,002,772 B2 * | 8/2011 | Sarin et al. | 606/53 |
| 8,192,449 B2 * | 6/2012 | Maier et al. | 606/151 |
| 2005/0113677 A1 * | 5/2005 | Davies et al. | 600/424 |
| 2005/0149050 A1 * | 7/2005 | Stifter et al. | 606/102 |
| 2007/0276370 A1 * | 11/2007 | Altarac et al. | 606/61 |

* cited by examiner

*Primary Examiner* — Kevin T Truong
*Assistant Examiner* — Christopher Beccia

(57) ABSTRACT

A percutaneous registration apparatus and method for use in minimally invasive spinal surgery. The apparatus including a holding member, first and second clamping members, first and second gripping members, and an adjustment mechanism for closing and opening the first and second gripping members.

12 Claims, 8 Drawing Sheets

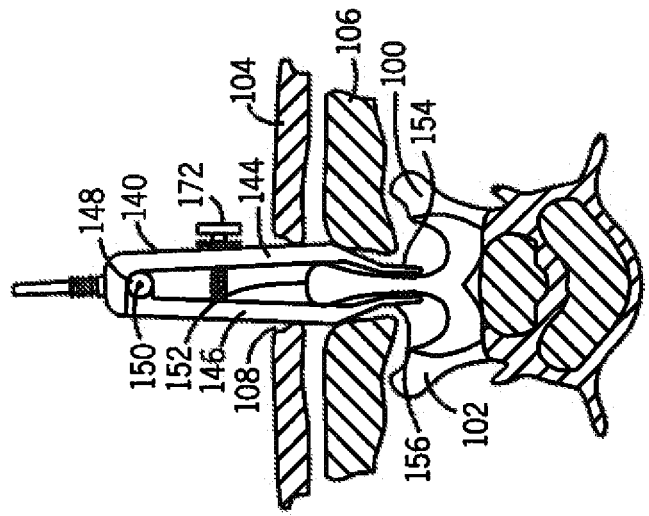
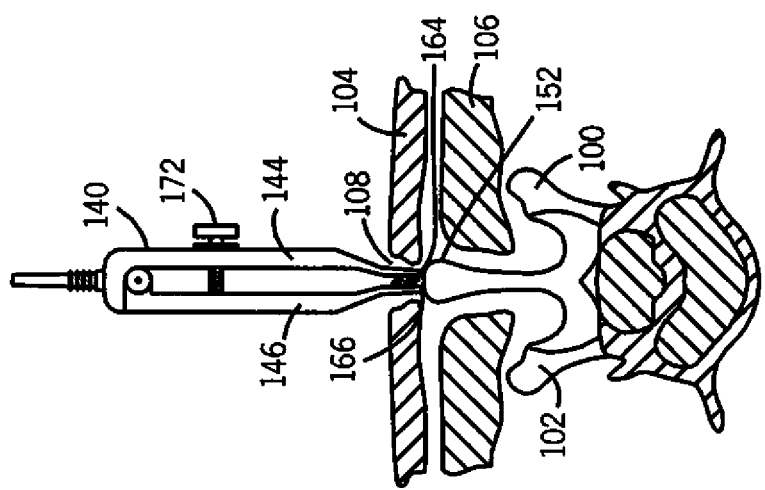
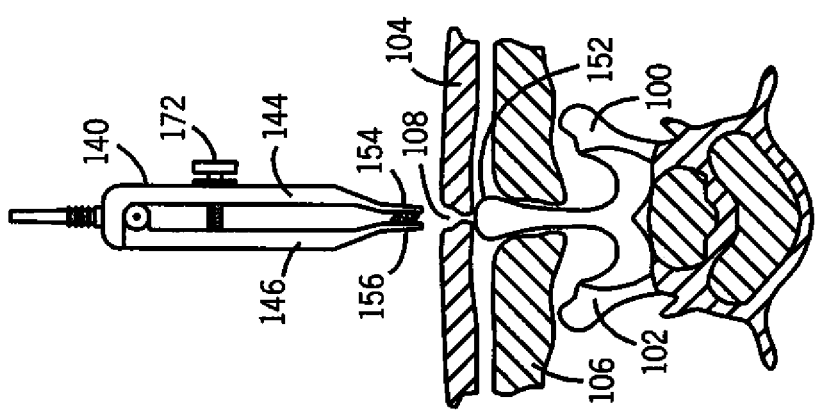

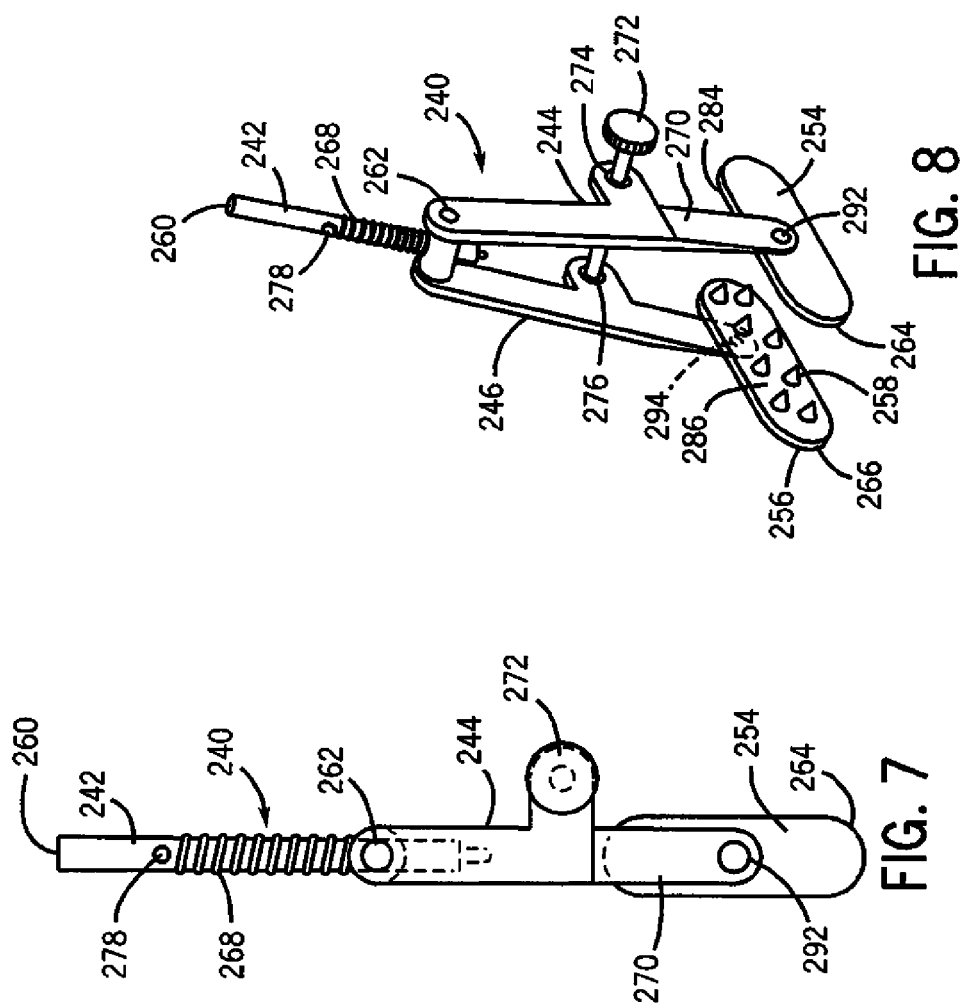

PERCUTANEOUS REGISTRATION APPARATUS AND METHOD FOR USE IN SURGICAL NAVIGATION

BACKGROUND OF THE INVENTION

This disclosure relates generally to image-guided surgery (or surgical navigation), and more particularly, to a registration apparatus and method for use in percutaneous spinal surgical navigation procedures with surgical navigation systems.

Surgical navigation systems track the precise location of surgical instruments in relation to multi-dimensional images of a patient's anatomy. Additionally, surgical navigation systems use visualization registration apparatus to provide the surgeon with co-registered views of these surgical instruments with the patient's anatomy.

Surgical procedures involving the spine typically require the formation of a relatively large incision through the skin of the patient adjacent the portion of the spinal column to be treated. The size of the surgical incision must be large enough to accommodate for the manipulation and/or placement of various surgical instruments and implants required for the surgical procedure. Additionally, if surgical navigation technology is to be used in association with the surgical procedure, the surgical incision must also accommodate the mounting of a dynamic reference or registration device to the spinal column. The dynamic reference or registration device is attached to the spinous process via a bone pin or clamp. For electromagnetic surgical navigation systems, an electromagnetic field generator or an electromagnetic sensor is typically attached to the registration device.

However, recent advances in surgical technology have led to many more minimally invasive surgical procedures being performed. One minimally invasive method for registering the spine is through the use of a small bone pin inserted through a small incision in the back and into a bone of the spinal column. This bone pin is often vulnerable to loosening from low-density bone such as in osteoporosis.

Relative motion between the dynamic reference or registration device and the patient can introduce imprecision into a navigation system. It is therefore important that the dynamic reference or registration device be securely and rigidly mounted to the patient while also being minimally invasive. A problem with conventional dynamic reference devices relates to their size, high-profile designs and inadequate methods of anatomical attachment. Conventional dynamic reference devices are large enough to potentially limit surgical access, their high-profile design poses an increased risk of unintentional contact or bumping, and the methods of anatomical fixation are prone to failure.

Therefore, it is desirable to provide apparatus and methods for mounting a surgical navigation registration device to the patient in a minimally invasive manner to reduce the size of the surgical incision, or by eliminating the surgical incision entirely in applications involving percutaneous surgical procedures.

BRIEF DESCRIPTION OF THE INVENTION

In an embodiment, a registration apparatus for minimally invasive spinal surgery comprising a holding member, and a pair of movable first and second clamping members coupled to one end of the holding member. The holding member including a pair of first and second gripping members extending from the ends of the pair of movable first and second clamping members.

In an embodiment, a percutaneous spinal registration apparatus for minimally invasive spinal surgery comprising a holding member, first and second clamping members, first and second gripping members, and an adjustment mechanism for adjusting the angle between the holding member and the first and second clamping members, and for closing and opening the first and second gripping members.

Various other features, objects, and advantages of the invention will be made apparent to those skilled in the art from the accompanying drawings and detailed description thereof.

BRIEF DESCRIPTION OF THE DRAWINGS

FIG. 3 is an exemplary cross-sectional diagram of a spinal column with a front view of an embodiment of a registration apparatus shown above the spinal column prior to entering a percutaneous opening in the skin and engaging a vertebrae;

FIG. 4 is an exemplary cross-sectional diagram of a spinal column with a front view of an embodiment of a registration apparatus shown entering a percutaneous opening in the skin and engaging a vertebrae;

FIG. 5 is an exemplary cross-sectional diagram of a spinal column with a front view of an embodiment of a registration apparatus shown engaging a vertebrae;

FIG. 7 is an exemplary side view diagram of an embodiment of a registration apparatus;

FIG. 8 is an exemplary perspective view diagram of the embodiment of the registration apparatus shown in FIG. 7;

DETAILED DESCRIPTION OF THE INVENTION

In minimally invasive surgical (MIS) procedures, access to the body is obtained through one or more natural openings or small percutaneous incisions. Medical devices or implants are inserted through these openings and directed to a region of interest within the body. Direction of the medical devices or implants through the body is facilitated by navigation technology wherein the real-time location of a medical device or implant is measured and virtually superimposed on an image of the region of interest. The image may be a pre-acquired image, or an image obtained in near real-time or real-time using known imaging technologies such as computed tomography (CT), magnetic resonance (MR), positron emission tomography (PET), ultrasound, X-ray, or any other suitable imaging technology, as well as any combinations thereof.

Anchoring an image navigation dynamic reference device or a registration apparatus to at least one of the vertebrae is required prior to performing surgical navigation of spinal surgery. A registration apparatus is typically anchored to the vertebrae via a bone clamp having at least two opposing blades or jaws which include inwardly facing pointed tips or spikes that provide secure engagement with the vertebral bone. The blades or jaws are clamped about the spinous process of the vertebrae to maintain the dynamic reference device in a substantially fixed position relative to the vertebra. The blades are sized to receive the bulb-shaped portion of the spinous process therebetween and the spikes are configured to penetrate into bone tissue for secure fixation thereto.

An electromagnetic transmitter or receiver is coupled to the previously attached registration apparatus and images from two or more different views are taken and stored in an imaging and/or a navigation system. Through the use of a calibration device and the navigation system, the images are automatically registered to the patient's anatomy. During an MIS procedure, a surgeon is able to use these saved and calibrated images to plan trajectories, locate difficult anatomy, and determine other surgical parameters in near real-time using virtual instruments or implants superimposed over the previously saved images, with out the need for continuously updated fluoroscopic images.

Figure 1:
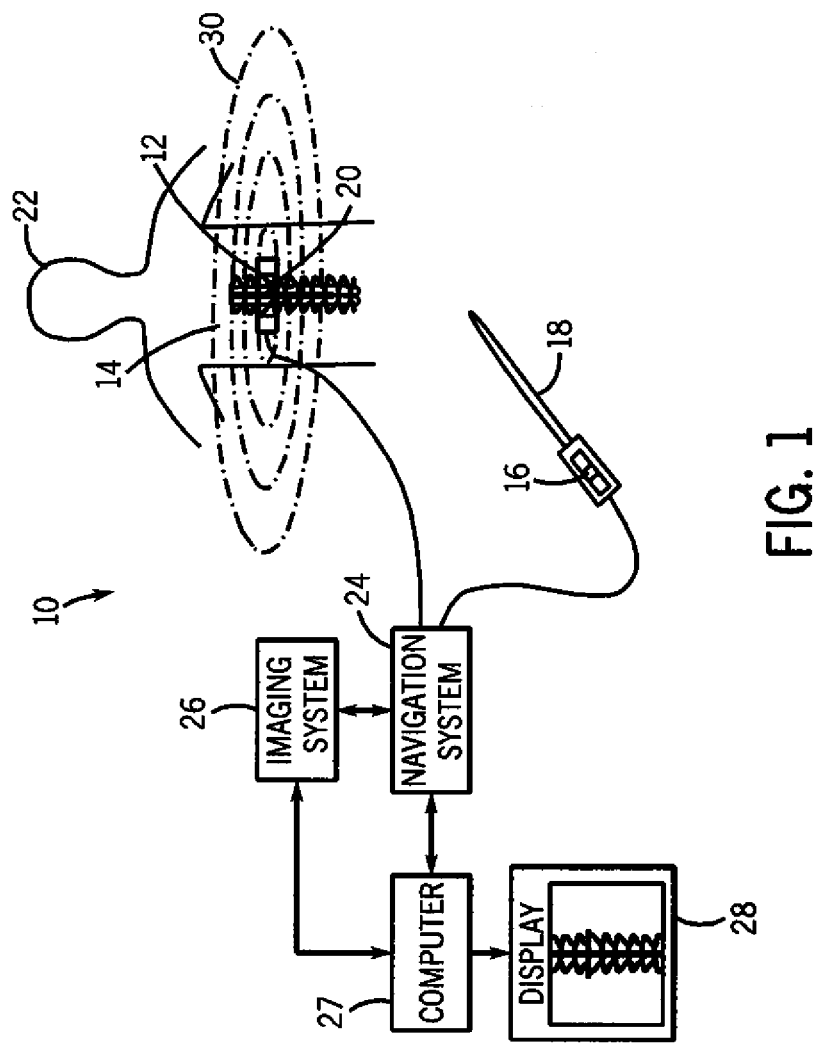
FIG. 1 is an exemplary schematic diagram of an embodiment of an imaging and navigation system.

Referring now to the drawings, FIG. 1 is an exemplary schematic diagram of an embodiment of an imaging and navigation system 10. The system 10 includes at least one electromagnetic field generator 12 positioned proximate to a surgical field of interest 14, at least one electromagnetic sensor 16 attached to at least one medical device 18 for communicating with and receiving data from the at least one electromagnetic field generator 12, a navigation system 24 coupled to and receiving data from the at least one electromagnetic sensor 16 and the at least one electromagnetic field generator 12, an imaging system 26 coupled to the navigation system 24 for performing imaging on a patient 22 in the surgical field of interest 14, a computer 27 coupled to the navigation system 24 and the imaging system 26, and a display 28 coupled to the computer 27 for displaying imaging and tracking data from the imaging system 26 and the navigation system 24. The at least one electromagnetic field generator 12 may be attached to a registration apparatus 20 that is attached to the patient 22 in the surgical field of interest 14. The at least one electromagnetic field generator 12 attached to the registration apparatus creates a local reference frame for the navigation system 24 around the patient's anatomy in the surgical field of interest 14. In another exemplary embodiment, the imaging system 26 and the navigation system 24 may be integrated into a single integrated imaging and navigation system with integrated instrumentation and software.

The system 10 enables a surgeon to continually track the position and orientation of the medical device 18 during surgery. An electromagnetic field 30 is generated around the at least one electromagnetic field generator 12. The at least one electromagnetic sensor 16 detects the electromagnetic field 30 generated by the at least one electromagnetic field generator 12 attached to the registration apparatus 20. The at least one electromagnetic sensor 16 may be an electromagnetic field receiver. The electromagnetic field receiver may be a receiver array including at least one coil or at least one coil pair and electronics for digitizing magnetic field measurements detected by the receiver array. The at least one electromagnetic field generator 12 may be an electromagnetic field transmitter. The electromagnetic field transmitter may be a transmitter array including at least one coil or at least one coil pair. It should, however, be appreciated that according to alternate embodiments the registration apparatus 20 may include at least one electromagnetic field receiver attached thereto and the medical device 18 may include at least one electromagnetic field transmitter attached thereto.

The magnetic field measurements can be used to calculate the position and orientation of the medical device 18 according to any suitable method or system. After the magnetic field measurements are digitized using electronics, the digitized signals are transmitted from the at least one electromagnetic sensor 16 to the navigation system 24. The digitized signals may be transmitted from the at least one electromagnetic sensor 16 to the navigation system 24 using wired or wireless communication protocols and interfaces. The digitized signals received by the navigation system 24 represent magnetic field information detected by the at least one electromagnetic sensor 16. The digitized signals are used to calculate position and orientation information of the medical device 18. The position and orientation information is used to register the location of the medical device 18 to acquired imaging data from the imaging system 26. The position and orientation data is visualized on the display 28, showing in real-time the location of the medical device 18 on pre-acquired or real-time images from the imaging system 26. The acquired imaging data from the imaging system 26 may include CT imaging data, MR imaging data, PET imaging data, ultrasound imaging data, X-ray imaging data, or any other suitable imaging data, as well as any combinations thereof. In addition to the acquired imaging data from various modalities, real-time imaging data from various real-time imaging modalities may also be available.

The navigation system 24 is illustrated conceptually and may be implemented using any combination of dedicated hardware boards, digital signal processors, field programmable gate arrays, and processors. Alternatively, the navigation system 24 may be implemented using an off-the-shelf computer with a single processor or multiple processors, with the functional operations distributed between processors. As an example, it may be desirable to have a dedicated processor for position and orientation calculations as well as a processor for visualization operations. The navigation system 24 may be an electromagnetic navigation system utilizing electromagnetic navigation technology. However, other tracking or navigation technologies may be used.

Figure 2:
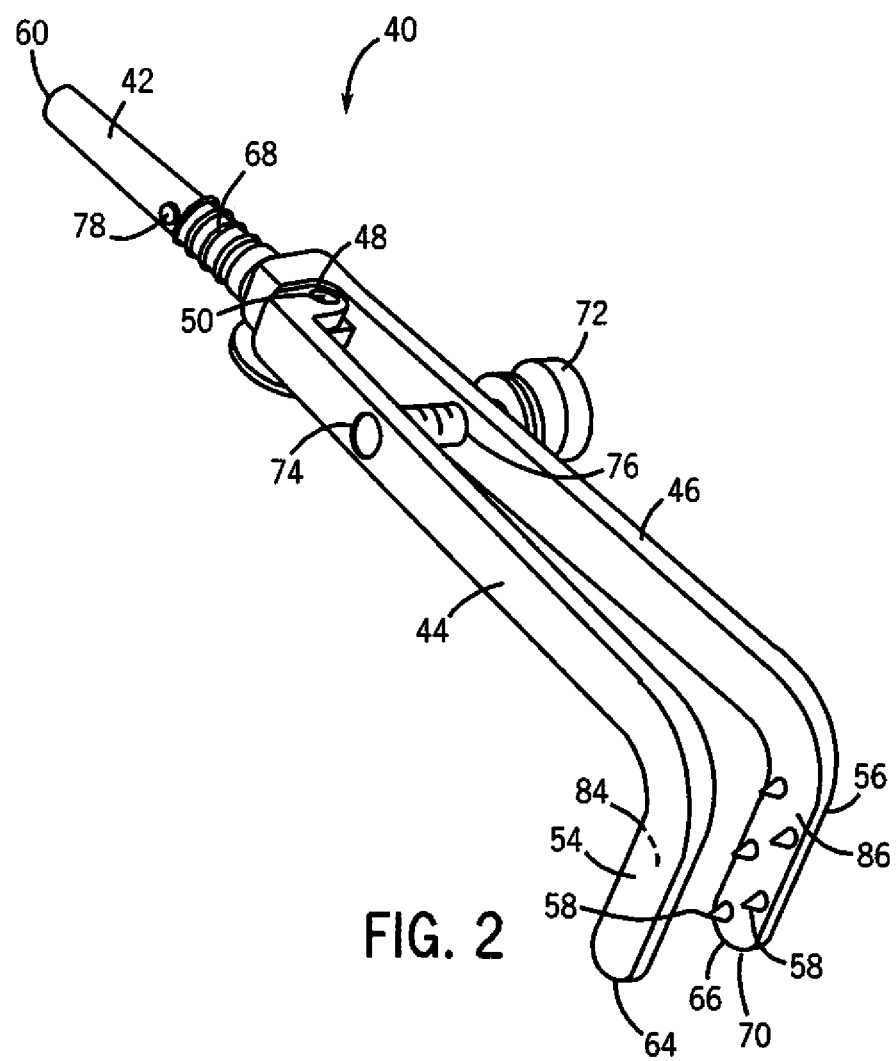
FIG. 2 is an exemplary perspective view diagram of an embodiment of a registration apparatus.

FIG. 2 is an exemplary perspective view diagram of an embodiment of a registration apparatus 40. In this embodiment, the registration apparatus 40 is a small right-angled registration apparatus that is designed for MIS spinal procedures having a 1 to 2 centimeter midline incision to the spinous process, and for the specific or general purpose of surgical registration and computer-assisted navigation. The registration apparatus 40 is removably attachable to the spinous process and includes at least one electromagnetic field generator or at least one electromagnetic sensor that is removably attachable to the registration apparatus.

The registration apparatus 40 includes a holding member 42 at a proximal end 60 thereof, configured for holding at least one electromagnetic sensor or at least one electromagnetic field generator thereto, and a pair of first 44 and second 46 clamping members at a distal end 70 thereof, that are attached to one end of the holding member 42 by a hinge mechanism 48 that is configured as a pivot point 50 for allowing the first 44 and second 46 clamping members to be movable between closed and open positions.

Herein, "proximal" refers to the potion of the registration apparatus which is typically closest to the surgeon during surgery or, alternatively, the portion of the registration apparatus which is protruding from the body during surgery. Thus, the proximal end of the registration apparatus is the portion of the registration apparatus which protrudes from the body during use. Conversely, "distal" refers to the portion of the registration apparatus which is typically furthest away from the surgeon during surgery or, alternatively, the portion of the registration apparatus which is typically and primarily inside the body during use.

The first 44 and second 46 clamping members each include a pair of first 54 and second 56 gripping members extending from the ends of the first 44 and second 46 clamping members, opposite from the pivot point 50, at approximately a right angle. The first 44 and second 46 clamping members extend a few inches above the first 54 and second 56 gripping members to clear the subcutaneous tissue it is inserted through as well as the incision that is likely to be 1 to 2 centimeters in length. The first 54 and second 56 gripping members each include a plurality of small pointed spikes 58 extending from an inner surface 84, 86 of each of the first 54 and second 56 gripping members, respectively, to penetrate into bone tissue for secure fixation of the registration apparatus 40 to the spinous process. The first 54 and second 56 gripping members also having blunt ends 64, 66, respectively, that can be used to gently pass through soft tissue and as a dissection device.

The first 44 and second 46 clamping members each include an internally threaded hole 74, 76, respectively, extending therethrough for receiving a threaded screw 72 therein for closing and opening the first 44 and second 46 clamping members, and the first 54 and second 56 gripping members about the hinged pivot point 50. Turning the screw 72 in a clockwise direction moves the first 44 and second 46 clamping members, and the first 54 and second 56 gripping members towards each other in a closed position. While turning the screw 72 in a counter clockwise direction moves the first 44 and second 46 clamping members, and the first 54 and second 56 gripping members away from each other in an open position.

The registration apparatus 40 further includes a spring 68 and a pin 78. The spring 68 is coupled around the holding member 42 above the first 44 and second 46 clamping members. The pin 78 extends through the holding member 42 above the spring 68 and is configured to hold the spring 68 in place around the holding member 42. The spring 68 and pin 78 both are used to secure a "keyed" hollow shaft of an electromagnetic field generator or an electromagnetic sensor reference device in place. The holding member 42 is also keyed. For example, a user slides a hollow electromagnetic field generator reference device shaft over the holding member 42, pin 78 and spring 68. As the hollow shaft is slid over the pin 78 and spring 68, the spring 68 is compressed and the user turns the hollow shaft 45 to 90 degrees to lock the shaft of the electromagnetic field generator or the electromagnetic sensor reference device in place on the holding member under the tension of the compressed spring 68 and locked by pin 78.

The registration apparatus 40 may be comprised of a material compatible with electromagnetic tracking technology, such a non-metallic material or a minimally conductive metal, so that the electromagnetic field 30 (shown in FIG. 1) is not distorted, and there is minimum disruption of the imaging technology. For example, the material may be a low ferrite alloy, such as titanium.

FIGS. 3-5 show an embodiment of a registration apparatus 140 in action. For discussion purposes, the use of the registration apparatus 140 is described with reference to FIGS. 3-5. Also for discussion purposes, particular components are indicated as performing particular functions. However, it is possible that other components (or combinations of components) may perform the particular functions.

FIG. 3 shows a lower portion of an embodiment of a registration apparatus 140 and a cross-section of a vertebra 100, particularly, its spinous process 102 and of tissue surrounding the spinous process 102. This tissue includes the skin and fascia 104, and the paraspinous muscles 106. As depicted in FIG. 3, there is a small incision 108 in the skin and fascia 104 through which the registration apparatus 140 may be inserted.

The registration apparatus includes first 144 and second 146 clamping members are hinged together by a hinge mechanism 148 at a pivot point 150 that allows the first 154 and second 156 gripping members to open and close without distracting the skin incision. The hinge mechanism 148 allows the first 154 and second 156 gripping members to be closed when passed through the skin and subcutaneous tissue to the spinous process 102. At this position, a surgeon can retract the first 154 and second 156 gripping members over the spinous process 102 until it is in position to be closed around the spinous process 102, as shown in FIGS. 4 and 5.

FIG. 4 shows the same elements as shown in FIG. 3, but the registration apparatus 140 is partially inserted into a patient's body. The blunt ends 164, 166 of the gripping members 154, 156 of the registration apparatus 140 are inserted through the small incision 108 in the skin and fascia 104. The surgeon aims the registration apparatus 140 so that the bulbous end 152 of the spinous process 102 goes in between the gripping members 154, 156. Once in position, the gripping members 154, 156 are closed to engage the spinous process 102.

FIG. 5 shows the same elements as shown in FIGS. 3 and 4, but the registration apparatus 140 is fully inserted into the patient's body. As depicted, the bulbous end 152 of the spinous process 102 is received by the cavity between the first 144 and second 146 clamping members of the registration apparatus 140, and the spinous process 102 is gripped by the first 154 and second 156 gripping members. The cavity between the first 144 and second 146 clamping members is designed to receive the bulbous end 152 of the spinous process 102. The first 154 and second 156 gripping members grip and stabilize the registration apparatus 140. As depicted, the first 154 and second 156 gripping members may extend to the base of the spinous process 102. However, under differing conditions (e.g., variations in human anatomy) and with different embodiments, the first 154 and second 156 gripping members might not extend all the way down to the base of the spinous process 102.

The entire insertion technique is performed in a "letter opening style," that is the blunt ends 164, 166 of the first 154 and second 156 gripping members enter the incision with the surgeon's hand and the first 144 and second 146 clamping members horizontal to the patient's back. Once the first 154 and second 156 gripping members are through the skin and fascia 104 and the paraspinous muscles 106, the first 144 and second 146 clamping members are elevated to a vertical position and the first 154 and second 156 gripping members are clamped around the spinous process 102.

When the surgeon wishes to remove the registration apparatus 140, he or she simply manually extracts it. The registration apparatus 140 is not affixed to the spinous process 102 in a permanent manner like would be the case for an invasive (e.g., screw, staple, etc.) or chemical (e.g., adhesive) attachment mechanism. Instead, the registration apparatus 140 is only "gripping" the spinous process 102. As such, the surgeon opens the first 144 and second 146 clamping members, and the first 154 and second 156 gripping members by unscrewing the screw 172. The registration apparatus 140 is then easily extracted.

Figure 6:
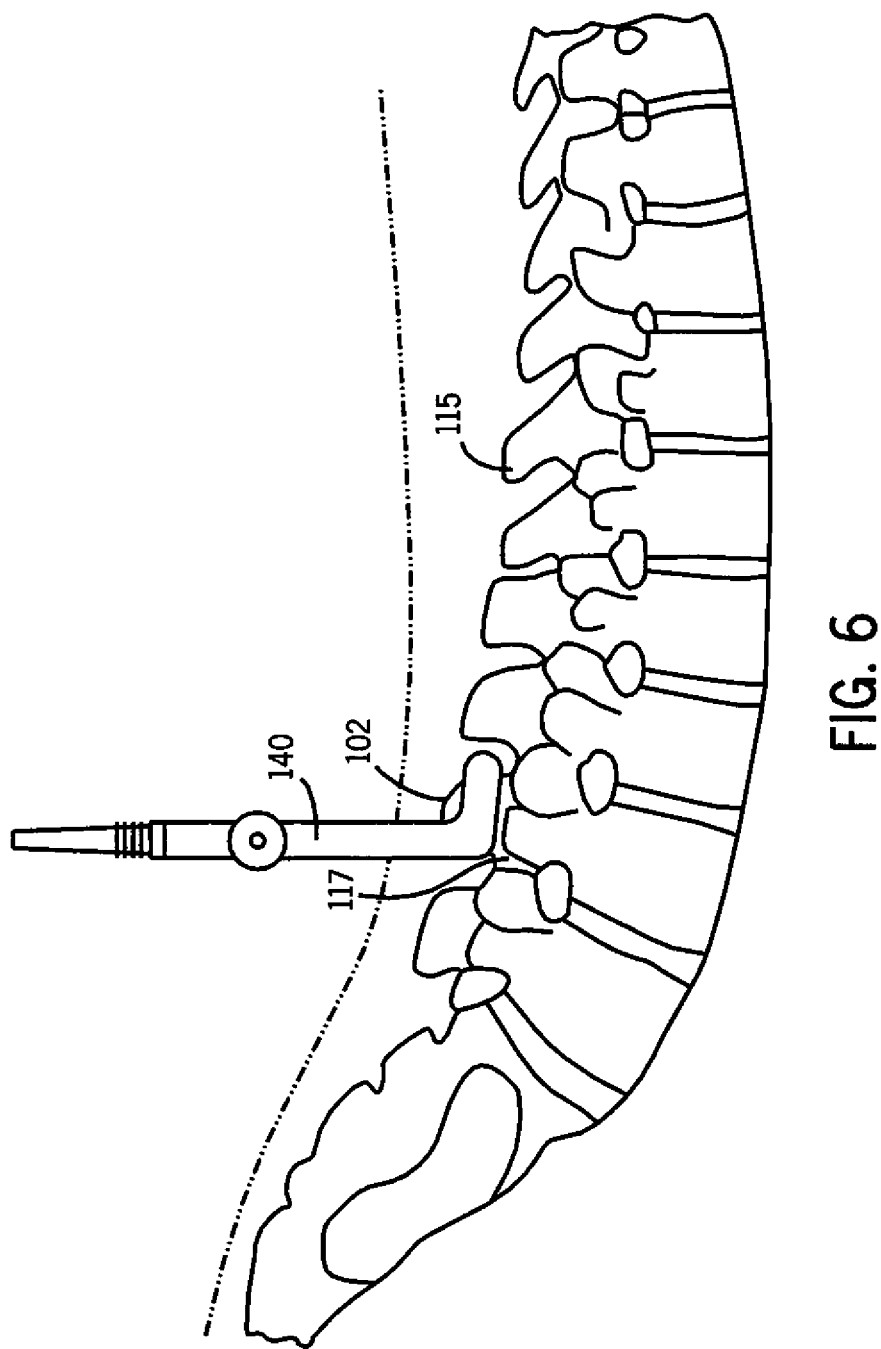
FIG. 6 is an exemplary enlarged side view diagram of a portion of a spinal column with an embodiment of a registration apparatus engaging a vertebrae.

FIG. 6 is an enlarged side view diagram of a portion of a spinal column 115 with a registration apparatus 140 engaging a vertebrae 117 according to an embodiment. FIG. 6 shows a side view of the registration apparatus 140 attached to a spinous process 102 of a vertebra 117.

FIG. 7 is an exemplary side view diagram of an embodiment of a registration apparatus 240. FIG. 8 is an exemplary perspective view diagram of the embodiment of the registration apparatus 240 shown in FIG. 7. In these embodiments, the registration apparatus 240 is a small straight registration apparatus that is designed for MIS spinal procedures having a 1 to 2 centimeter midline incision to the spinous process, and for the specific or general purpose of surgical registration and computer-assisted navigation. The registration apparatus 240 is removably attachable to the spinous process and includes at least one electromagnetic field generator or at least one electromagnetic sensor that is removably attachable to the registration apparatus.

The registration apparatus 240 includes a holding member 242 at a proximal end 260 thereof, configured for holding at least one electromagnetic sensor or at least one electromagnetic field generator thereto, at least one adjustment mechanism 262, a pair of first 244 and second 246 clamping members extending downwardly from the at least one adjustment mechanism 262, and a pair of first 254 and second 256 gripping members rotatably attached to the first 244 and second 246 clamping members at a distal end 270, thereof. In FIG. 7, the rotatable first 254 and second 256 gripping members are shown extending downwardly from the first 244 and second 246 clamping members in a vertical position parallel with the first 244 and second 246 clamping members. In FIG. 8, the rotatable first 254 and second 256 gripping members are shown extending outwardly from the first 244 and second 246 clamping members in a somewhat horizontal position or at an angle with respect to the first 244 and second 246 clamping members.

The holding member 242 may be a hollow tubular member that accepts at least one electromagnetic sensor or at least one electromagnetic field generator attached thereto, and has a circular rim 282 that forms a tubular opening 288 which is wide enough to easily accommodate manual insertion of a bone pin driver and/or a bone pin therethrough. A lower portion of the holding member 242, below the at least one adjustment mechanism 262 defines a circular cavity 290 which is designed to receive the bulbous-shaped spinous process plateau between the first 244 and second 246 clamping members.

The at least one adjustment mechanism 262 is used for adjusting the angle between the holding member 242 and the first 244 and second 246 clamping members, and for closing and opening the first 254 and second 256 gripping members. The at least one adjustment mechanism 262 may comprise a first adjustment mechanism 263 and a second adjustment mechanism 265 as is best illustrated in FIG. 8. The first adjustment mechanism 263 is used for adjusting the angle between the holding member 242 and the first 244 and second 246 clamping members. The first adjustment mechanism 263 may be configured like a toothed hinge allowing a user to rotate the holding member 242 at various angles to position an electromagnetic field generator or an electromagnetic sensor reference device that is mounted to the holding member 242 at various angles with respect to the patient. The second adjustment mechanism 265 is used for closing and opening the first 244 and second 246 clamping members and the first 254 and second 256 gripping members. The second adjustment mechanism 265 is positioned just below the first adjustment mechanism 263. The second adjustment mechanism 265 may be configured as a mechanical screw that may be turned in a clockwise or counter-clockwise direction to close or open the first 254 and second 256 gripping members.

The second adjustment mechanism 265 may include an optional bone pin insertion and removal mechanism (not shown) to insert and remove a stabilizing bone pin into and from the spinous process. This bone pin insertion and removal mechanism may work in tandem with the second adjustment mechanism, and may be configured like a hybrid rack and pinion assembly in which a user can insert the bone pin or bone pin driver and vertically rotate it down into the top of the spinous process by turning the mechanical screw of the second adjustment mechanism 265, and at the same time closing the first 254 and second 256 gripping members. When removing the bone pin, the mechanical screw is turned in the opposite direction to open the first 254 and second 256 gripping members and retract the bone pin from the spinous process.

The rotatable first 254 and second 256 gripping members freely rotate about the ends of the first 244 and second 246 clamping members at a pivot point 292, 294 on each of the first 244 and second 246 clamping members. The first 254 and second 256 gripping members each include a plurality of small pointed spikes 258 extending from an inner surface 284, 286 of each of the first 254 and second 256 gripping members, respectively, to penetrate into bone tissue for secure fixation of the registration apparatus 240 to the spinous process. Each of the first 254 and second 256 gripping members also having at least one blunt end 264, 266 that can be used to gently pass through soft tissue and as a dissection device.

The registration apparatus 240 may be comprised of a material compatible with electromagnetic tracking technology, such a non-metallic material or a minimally conductive metal, so that the electromagnetic field 30 (shown in FIG. 1) is not distorted, and there is minimum disruption of the imaging technology. For example, the material may be a low ferrite alloy, such as titanium or stainless steel.

FIGS. 9-12 shows an embodiment of an exemplary registration apparatus 340 in action. For discussion purposes, the use of the registration apparatus 340 is described with reference to FIGS. 9-12. Also for discussion purposes, particular components are indicated as performing particular functions. However, it is possible that other components (or combinations of components) may perform the particular functions.

Figure 9:
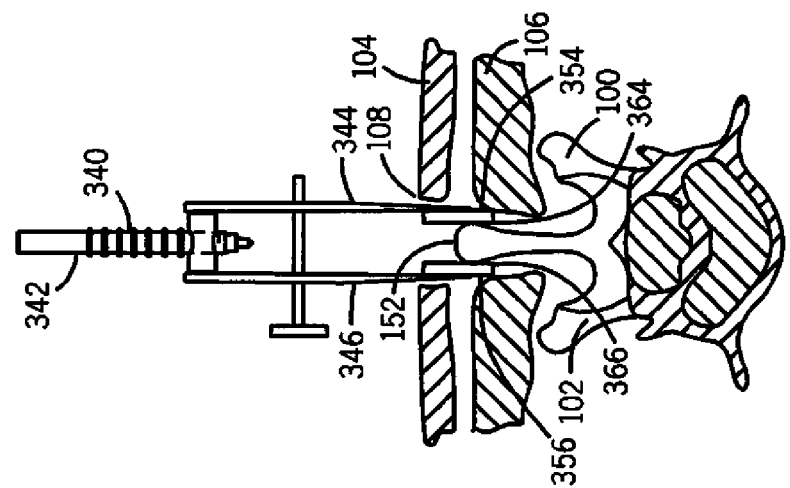
FIG. 9 is an exemplary cross-sectional diagram of a spinal column with a front view of an embodiment of a registration apparatus shown above the spinal column prior to entering a percutaneous opening in the skin and engaging a vertebrae.

FIG. 9 shows a lower portion of an embodiment of an exemplary registration apparatus 340 and a cross-section of a vertebra 100, particularly, its spinous process 102 and of tissue surrounding the spinous process 102. This tissue includes the skin and fascia 104, and the paraspinous muscles 106. As depicted in FIG. 9, there is a small incision 108 in the skin and fascia 104 through which the registration apparatus 340 may be inserted.

The registration apparatus 340 includes a holding member 342, an adjustment mechanism 362, first 344 and second 346 clamping members extending downwardly from the adjustment mechanism 362, and first 354 and second 356 gripping members rotatably attached to the ends of the first 344 and second 346 clamping members. The adjustment mechanism 362 allows the first 354 and second 356 gripping members to be closed when passed through the skin and subcutaneous tissue to the spinous process 102. The first 354 and second 356 gripping members also rotate from a vertical position to a horizontal position as the first 354 and second 356 gripping members are passed through the skin and subcutaneous tissue to the spinous process 102. A surgeon can retract the first 354 and second 356 gripping members over the spinous process 102 until it is in position to be closed around the spinous process 102, as shown in FIGS. 11 and 12.

Figure 10:
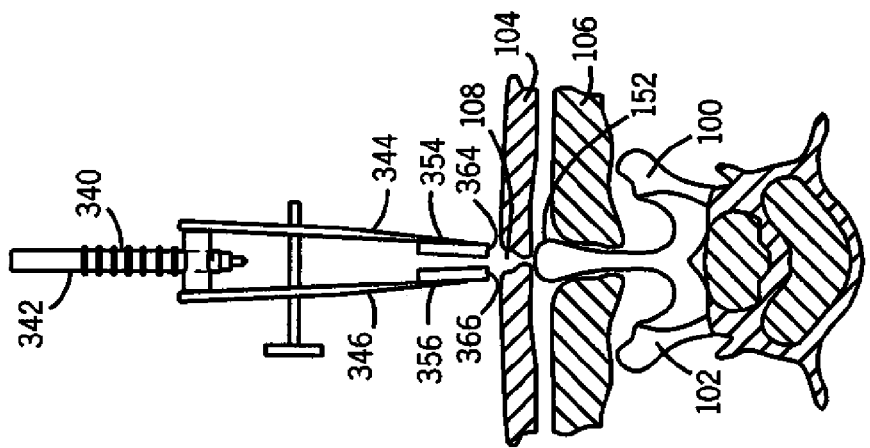
FIG. 10 is an exemplary cross-sectional diagram of a spinal column with a front view of an embodiment of a registration apparatus shown above entering a percutaneous opening in the skin and engaging a vertebrae.

FIG. 10 shows the same elements as shown in FIG. 9, but the registration apparatus 340 is partially inserted into a patient's body. The blunt ends 364, 366 of the gripping members 354, 356 of the registration apparatus 340 are inserted through the small incision 108 in the skin and fascia 104. The surgeon aims the registration apparatus 340 so that the bulbous end 152 of the spinous process 102 goes in between the gripping members 354, 356. Once in position, the gripping members 354, 356 are closed to engage the spinous process 102.

The first 344 and second 346 clamping members extend a few inches above the first 354 and second 356 gripping members to clear the subcutaneous tissue as it is inserted through as well as the incision that is likely to be 1 to 2 centimeters in length.

Figure 11:
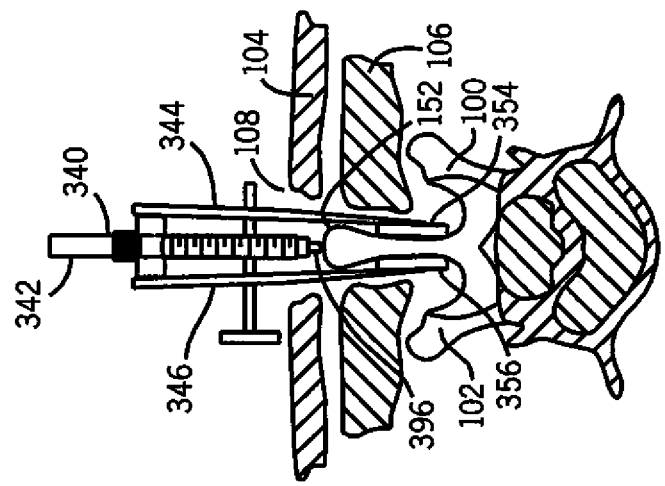
FIG. 11 is an exemplary cross-sectional diagram of a spinal column with a front view of an embodiment of a registration apparatus shown engaging a vertebrae.
Figure 12:
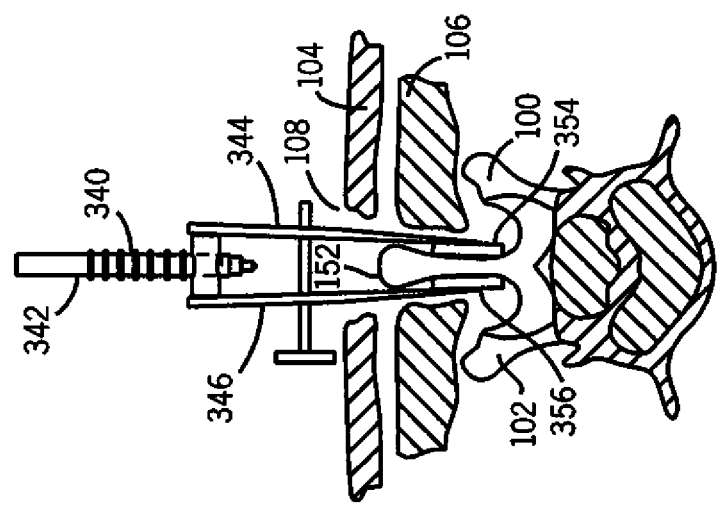
FIG. 12 is an exemplary cross-sectional diagram of a spinal column with a front view of an embodiment of a registration apparatus shown engaging a vertebrae and a bone pin extending through the registration apparatus and engaging a bone.

FIG. 11 shows the same elements as shown in FIGS. 9 and 10, but the registration apparatus 340 is fully inserted into the patient's body. As depicted, the bulbous end 152 of the spinous process 102 is received by the circular cavity 390 between the first 344 and second 346 clamping members of the registration apparatus 340, and the spinous process 102 is gripped by the first 354 and second 356 gripping members. The circular cavity 390 between the first 344 and second 346 clamping members is designed to receive the bulbous end 152 of the spinous process 102. The first 354 and second 356 gripping members grip and stabilize the registration apparatus 340. As depicted, the first 354 and second 356 gripping members may extend to the base of the spinous process 102. However, under differing conditions (e.g., variations in human anatomy) and with different embodiments, the first 354 and second 356 gripping members might not extend all the way down to the base of the spinous process 102.

FIG. 12 shows the same elements as shown in FIG. 11. Unlike the previous figures, FIG. 12 illustrates the use of the registration apparatus for one of its primary purpose (with at least one implementation). The registration apparatus 340 may also include a bone pin 396 able to resist bending to penetrate the spinous ligament and cortex of the superior spinous process plateau acting as a center fixation point for the registration apparatus 340 preventing slippage and wobble. As depicted, the bone pin 396 is shown inside of the holding member 342. This embodiment allows for seamless passage and access of a bone pin 396 and a bone pin driver 398 to the spinous process 102. The bone pin driver 398 may be threaded or non-threaded. With this access, the surgeon firmly affixes the bone pin 396 to the bulbous end 152 of the spinous process 102. The bone pin 396 functions to further stabilize the registration apparatus 340 from any movement. This bone pin 396 may be driven by rotation into the cortex when the gripping members 354, 356 are closed or used simply to penetrate the bone during downward forces.

The entire insertion technique is performed by inserting the blunt ends 364, 366 of the first 354 and second 356 gripping members through the incision with the surgeon's hand and the first 344 and second 346 clamping members vertical to the patient's back. Once the first 354 and second 356 gripping members are through the skin and fascia 104 and the paraspinous muscles 106, the first 354 and second 356 gripping members are opened to get around the bulbous end 152 of the spinous process 102, and closed around the lateral faces of the spinous process 102.

When the surgeon wishes to remove the registration apparatus 340, he or she simply manually extracts it. The registration apparatus 340 is not affixed to the spinous process 102 in a permanent manner like would be the case for an invasive (e.g., screw, staple, etc.) or chemical (e.g., adhesive) attachment mechanism. Instead, the registration apparatus 340 is only "gripping" the spinous process 102. As such, the surgeon opens the first 354 and second 156 gripping members and extracting registration apparatus 340.

Figure 13:
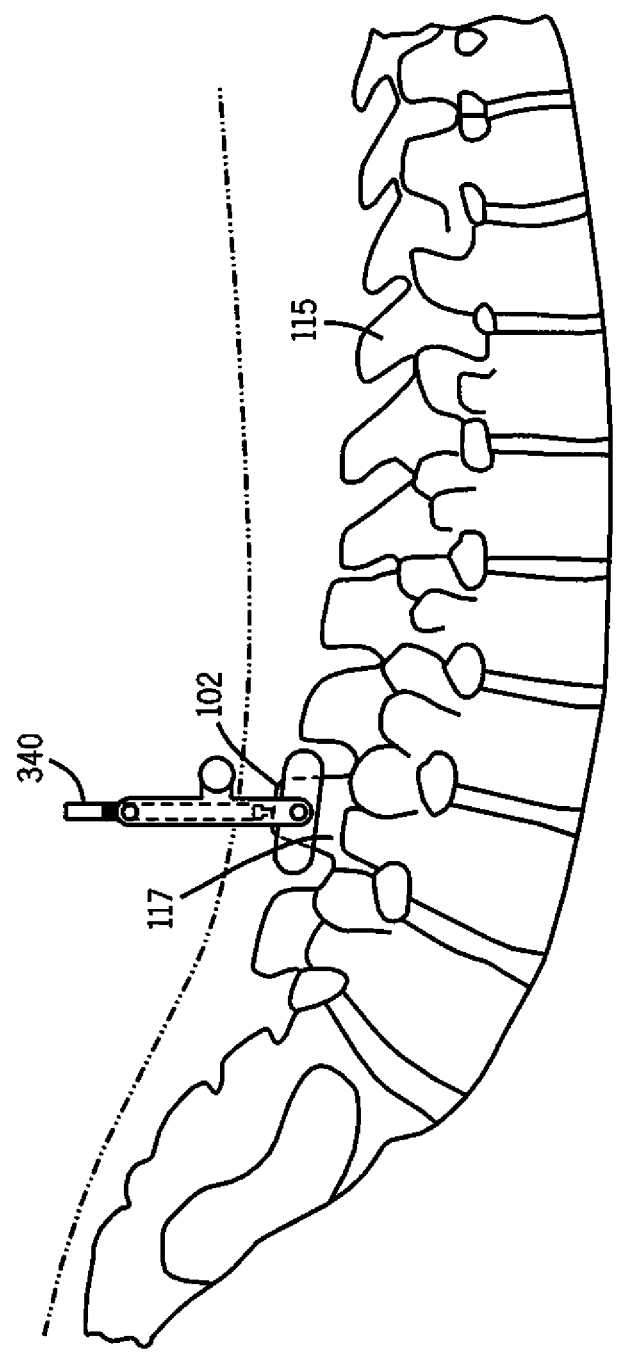
FIG. 13 is an exemplary enlarged diagram of a portion of a spinal column with an embodiment of a registration apparatus engaging a vertebrae.

FIG. 13 is an enlarged diagram of a portion of a spinal column 115 with a registration apparatus 340 engaging a vertebrae 117 according to an embodiment. FIG. 13 shows a side view of the registration apparatus 340 attached to a spinous process 102 of a vertebra 117.

In an embodiment, the registration apparatus may be utilized together with a tubular handle and/or a tubular sleeve dilator. The tubular handle may be attached to the holding member of the registration apparatus to carry the registration apparatus to the surgical site and assist in fixing the registration apparatus to the spinous process 102. The tubular sleeve dilator may be used to aid the registration apparatus through thick subcutaneous tissue when necessary. The tubular sleeve dilator is passed through the skin and subcutaneous tissue of thicker patients until it reaches the spinous process at the correct angle. Holding the tubular sleeve dilator in place, the gripping members of the registration apparatus are passed through the dilator to the spinous process in an open position. The gripping members are then tightened down, which opens and closes the gripping members and additionally may drive a bone pin into the plateau bulbous of the spinous process cortex to finalize the rigidity of the construct to the bone. The tubular handle and tubular sleeve dilator are then removed and the at least one electromagnetic sensor or at least one electromagnetic field generator is attached before or after the tubular sleeve dilator is removed depending on patient size.

The embodiments of a registration apparatus inserted through a percutaneous incision, maintains the minimal incision size required for the registration apparatus without extending the incision for a larger registration apparatus; allows a surgeon to quickly and easily attach at least one electromagnetic sensor or at least one electromagnetic field generator to the dorsal spine for quick registration; ensures a stronger grip decreasing the risk of loosing surgical registration between the anatomy and the navigated image; saves time in targeting the ideal entry point into the bone cortex for optimal angle and bone purchase; and saving valuable operating room set-up time, ease of use, robust navigation throughout the procedure, and multiple repositioning of the registration apparatus.

While the invention has been described with reference to several embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:
1. A registration apparatus for minimally invasive spinal surgery comprising:
a holding member;
a pair of movable first and second clamping members spaced apart from each other and coupled to one end of the holding member by a hinge mechanism that is con- figured as a pivot point for the pair of movable first and second clamping members; and a pair of first and second gripping members extending from the ends of the pair of movable first and second clamping members;

wherein the hinge mechanism and pivot point allow movement of the pair of movable first and second clamping members for movement of the first and second gripping members between an open position and a closed position; and wherein the pair of first and second gripping members extend from the ends of the pair of movable first and second clamping members at right angles.

2. The apparatus of claim 1, wherein the holding member is configured for holding at least one electromagnetic sensor or at least one electromagnetic field generator thereto.

3. The apparatus of claim 1, wherein the pair of first and second gripping members include a plurality of small pointed spikes extending from an inner surface of each of the first and second gripping members.

4. The apparatus of claim 1, wherein the pair of first and second gripping members each include at least one blunt end.

5. The apparatus of claim 1, wherein the pair of first and second clamping members each include an opening extending therethrough for receiving a mechanism for opening and closing the pair of first and second clamping members.

6. A percutaneous spinal registration apparatus for minimally invasive spinal surgery comprising:

a holding member;

first and second clamping members spaced apart from each other and coupled to one end of the holding member;

first and second gripping members coupled to the ends of the first and second clamping members; and at least one adjustment mechanism for allowing movement of the first and second gripping members between an open position and a closed position;

wherein the holding member includes a bone pin that is downwardly extendible between the first and second clamping members for fixation to a bulbous end of a spinous process.

7. The apparatus of claim 6, wherein the holding member is configured for holding at least one electromagnetic sensor or at least one electromagnetic field generator thereto.

8. The apparatus of claim 6, wherein the first and second clamping members extend downwardly from the holding member and the adjustment mechanism.

9. The apparatus of claim 6, wherein the first and second gripping members are rotatably attached to an end of the first and second clamping members.

10. The apparatus of claim 9, wherein the first and second gripping members rotate around a pivot point.

11. The apparatus of claim 6, wherein the first and second gripping members include a plurality of small pointed spikes extending from an inner surface of each of the first and second gripping members.

12. The apparatus of claim 6, wherein the first and second gripping members each include at least one blunt end.

* * * * *